Figure 1:
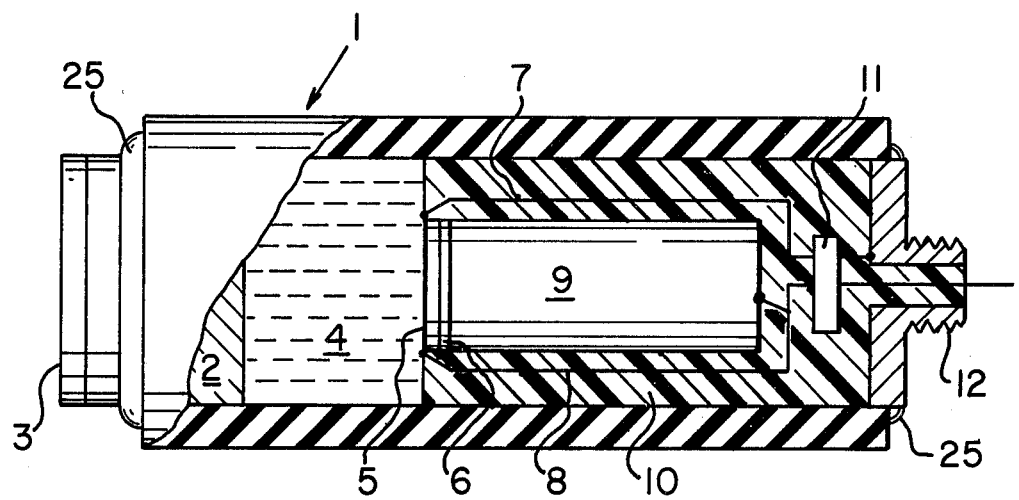

United States Patent

Mastandrea

[11] 4,073,193
[45] Feb. 14, 1978

[54] TRANSDUCER DEVICE

[76] Inventor: John R. Mastandrea, 8 Stirrup Road, Rancho Palos Verdes, Calif. 90274

[21] Appl. No.: 728,997

[22] Filed: Oct. 4, 1976

[51] Int. Cl.² .......................................... G01N 15/00
[52] U.S. Cl. ........................... 73/432 PS; 73/170 R; 73/DIG. 4; 310/334
[58] Field of Search ............. 73/71.4, 170 R, DIG. 4, 73/194 B, 432 PS; 310/8.7, 9.1

[56] References Cited

U.S. PATENT DOCUMENTS

| | | | |
|---|---|---|---|
| 3,159,029 | 12/1964 | Ruderman | 73/170 R |
| 3,179,823 | 4/1965 | Nesh | 310/8.7 X |
| 3,365,593 | 1/1968 | Roof et al. | 310/8.7 |
| 3,830,103 | 8/1974 | Andrejkovics | 73/170 R |
| 3,844,174 | 10/1974 | Chabre | 73/432 PS |

FOREIGN PATENT DOCUMENTS 1,254,493  11/1971  United Kingdom ............. 73/432 PS

OTHER PUBLICATIONS

Modlo et al., "Ultrasonic Pressure & Frequency Analyzer"- IBM Technical Disclosure Bulletin- vol. 14, No. 3, Aug. 1971, pp. 850-851.

Primary Examiner—Charles A. Ruehl
Attorney, Agent, or Firm—Webb, Burden, Robinson & Webb

[57] ABSTRACT

A transducer device and a system incorporating said transducer device useful, for example, for measuring a characteristic of particles in a particle flow stream. The transducer device comprises a front surface solid element in which an elastic wave is created, for example, on impact of a particle on an exposed front surface; a liquid medium; a thin piezoelectric sensing element; a solid back surface element; and a housing to hold the front and back surface elements in spaced relation with the lqiuid medium therebetween. Elastic waves created at the front surface are propagated through the piezoelectric element. The acoustic configuration of the transducer device is such that the electrical output signal of the thin piezoelectric is indicative of some characteristic of the first and the fastest pulse of the elastic wave. Systems including the transducer device comprise circuitry for processing the output of the piezoelectric transducer including, for example, amplifiers, filters, peak detectors, counters, rate meters, zero crossing detectors, etc. which provide an output characteristic, for example, of number, momentum, energy, mass, size and/or velocity of particles striking the front surface.

16 Claims, 2 Drawing Figures

TRANSDUCER DEVICE

This invention relates to piezoelectric acoustic and ultrasonic transducer devices. The invention relates to transducer devices which may be used to measure the number, energy, momentum, mass and size of particles impacting a surface or to measure elastic waves (acoustic or ultrasonic) generated internally or externally in another material. More particularly, the invention relates to measurements at very high rates of impacts (typically at a million impacts per second) and/or at very high impact speeds.

This invention relates to transducer devices for general purpose use as an instrument for impact measuring and elastic wave measuring, but can be used to solve at least six specific problems as follows:

1. Detection and measurement of erosive materials that impact on reentry vehicles and missiles in a flight environment.
2. Measurement of the time history of the number flux and particle size of erosive particles put into a flow stream at an erosion test facility. Currently, these facilities can only measure particle size and mass a few times during a test run using a pulsed laser optical system.
3. Detection of meteoroid and/or orbital debris impacts on satellites or space vehicles. Measurement of impacting particle size, momentum, mass and energy is important in both space structure design and knowledge of the meteoroid environment.
4. Measurement of particle materials in a pipe in a production flow of oil or gas from a well.
5. Measurement of energy releases (commonly called acoustic emissions) internally in a material or structure that occurs during material stressing at a defect location or during seismic activity.
6. Movement monitoring of a liquid medium.

Prior to my invention several types of devices had been used or proposed for solution of these problems. Two of the most commonly used types of erosion measuring probes are described: One device uses an ultrasonic piezoelectric transducer bonded to the rear surface of a material whose front surface is being eroded. The transducer is designed to send an ultrasonic wave pulse propagating through the material to the front surface of the material and then to detect the wave pulse reflected back to the transducer. By measuring the total transit time of the propagated wave through the material, the erosion depth can be obtained. A second device is one coated with a radioactive material and placed in an erosive stream. As the particle material erodes away the radioactive material, the radioactive reading of the probe changes. See for example, U.S. Pat. No. 3,678,273.

Another known device is an acoustical instrument, such as piezoelectric crystal pickup bonded to the outside of a pipe. See, for example, U.S. Pat. No. 3,580,092.

For particle impact detection, a number of devices have been proposed. One such device is disclosed in U.S. Pat. No. 3,816,773 where a probe with a piezoelectric crystal is installed in a pipe for monitoring of particles in oil or gas flowing from a well. Some consideration has been given to various aspects of the acoustic configurations of acoustic devices. See, for example, U.S. Pat. Nos. 2,430,013; 3,376,438; 3,497,728; 3,794,866 and 3,844,174.

This invention has a number of advantages over prior devices. An advantage of the invention is that it can provide accurate detection and measurement of a characteristic of the impacted particle. It can provide improved accuracy and linearity at very high rates of impacts and/or at very high impact speeds such that the measured parameter (e.g., number, rate, energy, momentum, mass and size) is representative of impacting materials. Also, the transducer device can operate in noisy, high vibration, high turbulence, high temperature, and wide pressure range environments.

Briefly, according to this invention, there is provided a transducer device in which the first and fastest elastic wave generated at the front surface of the transducer device is transmitted through a piezoelectric transducer. This is accomplished by propagating the fastest wave through the transducer device with much less attenuation than other waves generated at the front surface. The effects of external environments are attenuated or reduced significantly so that the transducer has a low background noise level.

The transducer device consists basically of a front surface solid element, a liquid medium, a piezoelectric sensing element, a solid back surface element, damping material and a housing to join the front surface element to the back surface element. An impacting particle gives up energy upon striking the front surface element. Elastic waves are generated at a location on the front face of the front surface element. The combined effects of the controlled elastic wave attenuation properties of the front and back surface elements, the liquid medium that does not allow transmission of the transverse elastic wave, and the small thickness piezoelectric sensing element result in a novel transducer device whose output signal is representative of a characteristic of the particle that impacted the front face. The transducer device may be used in a system comprising circuitry which consists of amplifiers, filters, peak detectors, counters, rate meters, zero crossing detectors, and converters to provide a continuous real time processing of signal output for number, momentum, energy, mass and particle size. The output signal can also be recorded directly on a wide band tape recorder and played back into a digital computer or signal processor for a more comprehensive analysis.

Figure 2:
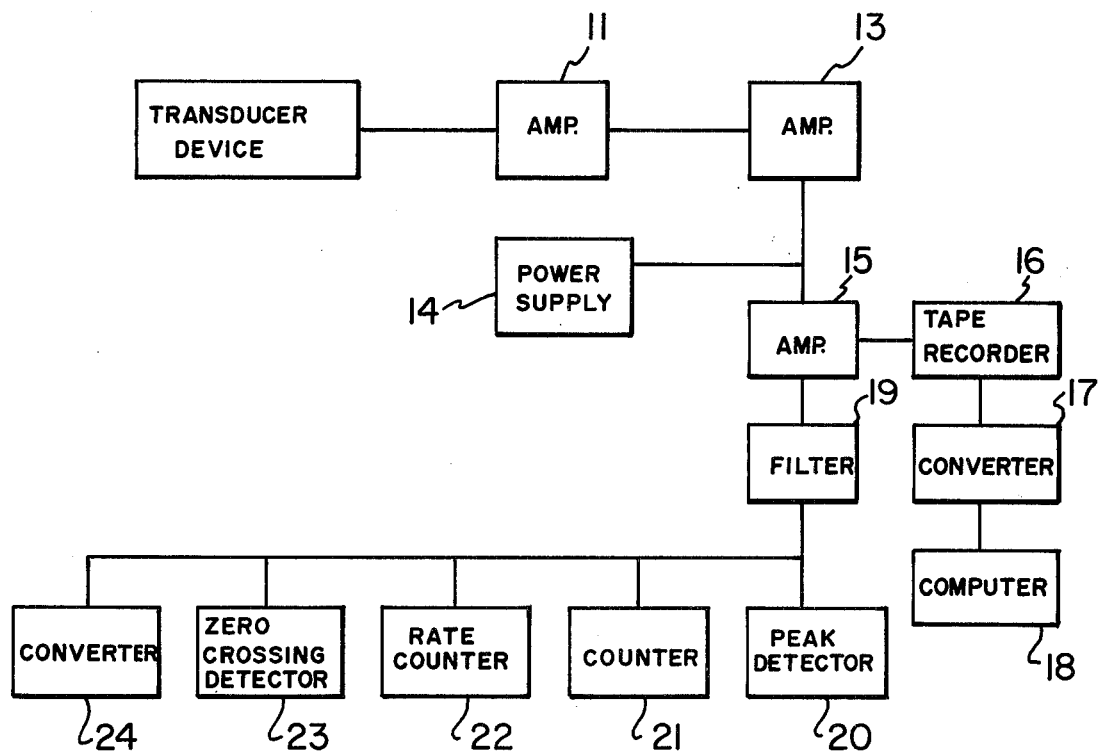

Further features and other objects and advantages of this invention will become apparent from the following detailed description in which:

FIG. 1 is a schematic diagram of a transducer device according to this invention, and FIG. 2 is a block diagram illustrating a system in which the transducer device according to this invention may be used.

Referring now to FIG. 1, the transducer device comprises a generally cylindrical housing 1 typically less than two centimeters in diameter and fifteen centimeters in length. The housing should comprise a solid material with a low acoustic impedance, low wave propagation rate (velocity) and high wave attenuation properties. The housing should generally be as thin as possible particularly between the transducer front surface element 2 and sensing element 5. A thin-walled rubber tubing, such as a shrink tube, is one of the preferred structures that can be used for the housing.

The front surface element 2 of the transducer device should be rugged because it is typically placed in the particle flow for the best measurement. The front surface element 2 can be protected by a thin strong wear surface material 3, for example, aluminum bonded or attached to the front surface or a thin coating of a wear resistance material, for example, titanium carbide.

In other applications, the front surface element 2 is coupled to the surface of another material or structure by pressure (hand held or mechanical) with or without a coupling liquid or grease. This other material or structure is one that is either impacted externally or generates acoustic waves internally, for example, under stress and due to internal defects.

The front surface element 2 is a controlled elastic wave propagating medium for the elastic waves that are generated on the front surface. Front surface element 2 should be a solid that typically has a high elastic wave attenuation characteristic and as low an acoustic impedance characteristic as possible considering the other requisite properties. The high wave attenuation characteristic will provide that the initial longitudinal wave (caused by a particle impact or passed on from another material or structure in contact with front surface) will propagate through the back of the front surface material 2 into the adjacent liquid type medium 4 with much higher value than any reflected longitudinal waves, that is, with much higher value than any wave that reflects inside the front surface element 2 and eventually propagates through the back of the front surface element. A low acoustic impedance characteristic is preferred in order to provide closer impedance match at the interface with the adjacent medium. The closer the impedance match, the higher the value of the elastic wave propagated into the liquid medium. The length of the front surface element 2 depends upon a variety of test and environmental conditions such as impact velocity and dynamic pressures. A very long front surface element will tend to spread the longitudinal wave and increase its pulse period thus reducing the particle counting capability. Typically, the length of the element should range from 0.1 to 5 centimeters but could extend up to a meter in length.

The liquid type medium 4 is placed between the front surface element 2 and the sensing element 5. The liquid type medium 4, (e.g. grease, water, oil) is used to eliminate the propagation of transverse elastic waves in the front surface material 2 to the sensing element 5. Other materials such as rubber may be used for the liquid type medium 4 because they also do not propagate the transverse elastic waves. They are not preferred, however, because of the high longitudinal wave attenuation characteristics of the rubber-like materials. Also, these materials require application of a bonding material to each side for attachment to the front surface material 2 and sensing element 5. Bonding materials at these locations cause the initial longitudinal wave to be reduced in value and to be somewhat distorted. The length of the liquid medium is dependent on the particle impact conditions and the external test environment. It is preferred that the length of the liquid type medium is sufficiently long to damp out dynamic pressures such as those caused by external turbulence, or other environmental factors. The liquid medium 4 length is typically greater than 0.2 centimeters.

A thin piezoelectric sensing element 5 (e.g. $PENb_2O_6$, $BaTiO_3$, PZT) with metallic film deposited on both the front and back surface may be placed between the liquid type medium 4 and the back surface element 9. A very thin coating of epoxy 6 may be used to bond the piezoelectric sensing element 5 to the back surface material 9. Conductive epoxy is used if the back surface material is electrically conductive. Electrical leads 7 and 8 are attached to both sides of the piezoelectric sensing element, typically by conductive epoxy or solder. An electrical lead 8 is not required if the back surface material 9 is electrically conductive. Then a lead is attached at the rear of the back surface material 9. The piezoelectric sensing element 5 can advantageously be a piezoelectric plastic electret element such as tetrafluoroethylene, flourinated ethylene, and polyvinylfloride. These thin plastic materials produce output voltages as the elastic wave passes through them. A plastic electret material is preferred for a number of reasons. For one, they have a low acoustic impedance thus providing a good impedance match at the liquid medium 4 and sensing element 5 interface. This allows most of the energy to propagate from the liquid medium 4 through the piezoelectric sensing element 5. Another reason is that the initial transverse wave set up in the thin sensing element 5 is of extremely high frequency and can easily be discriminated from the longitudinal elastic waves that propagate through the length of the transducer. External vibration waves, that is, those not generated from the particle impact, are generally low frequency. These, also, can be easily discriminated from the longitudinal elastic waves.

The back surface element 9 of the transducer is an elongate solid material that can be electrically conductive or nonconductive. The back surface material 9 is used as a controlled elastic wave propagation medium. It is a solid material chosen to highly attenuate the elastic wave as the wave propagates through it. In this way, waves reflected from the back surface are highly attenuated before returning through the sensing element 5. The back surface element 9 is also chosen to provide a good impedance match with the sensing element 5 so that most of the energy of the elastic wave travels through the sensing element into the back surface element 9. Very little energy will be reflected back through the sensing element 5 at the sensing element 5 and back surface element 9 interface. The back surface material 9 can also be a combination of different types of material to accomplish the controlled propagation of the elastic wave. Typically, the length of the back surface material 9 is a few centimeters. However, it can vary from a few millimeters to meters in length. Typical materials such as zinc, lead, plastics, rubber, plexiglass can be used for the back surface material 9.

An optional damping material 10 bonds to or is attached to the outside surface of the back surface element 9 and inside the external housing 1. The damping material 10 further controls the elastic wave propagated at impact and also external acoustical waves. The material can be solid or liquid material such as epoxy, grease, RTV, etc.

Sealing 25 of the external housing 1 and the front surface element 2 and back surface element 9 is optional and can be accomplished by, for example, epoxy resin bonding or taping.

Referring now to FIG. 2, the transducer device may be used in a system. Depending upon such factors as (1) the output signal level required (2) background vibrations and noise and sensing measurement desired, an amplifier 11 can be installed inside the transducer device between electrical lead 7 and the center conductor electrical lead 8 or an external amplifier 13 can be connected to the external connector 12 which is a part of the transducer device housing 1. The amplifiers 11 or 13 can be used to condition the transducer output signal for recording. For many applications (e.g. where piezoelectric crystals are used) the amplifiers 11 or 13 are not required. The amplifiers 11 or 13 can be any one of several commercially available impedance converters such as Kistler Model 557 amplifier. The amplifier is used to eliminate the unwanted noise effect of the cable movement external to the transducer and also to reduce the effect of signal output attenuation by the capacitance of external cables. This is done because the amplifiers 11 or 13 convert the high impedance output of the transducer 6 to a low impedance output. A chip integrated circuit is also available from PCB Corporation for installation inside the transducer housing as an amplifier 11. The amplifiers 11 or 13 are powered by a constant current power supply 14. The unit is commercially available (e.g. Kistler Model 568). Either the output of amplifier 11 or 13 or the unamplified transducer output at connector 12 is then amplified by commercially available amplifiers 15, e.g., differential, wideband, or operational types (such as Fairchild u715). The output voltage is multipiled by the gain of the amplifier 15 which typically ranges from one to one hundred thousand.

Systems according to this invention may process the output signal in one of the following ways. The amplifier signal may be recorded on a wideband tape recorder 16 and then played back into a digital processor 17 and computer 18 for comprehensive data processing. Numerous commercial digital processors 17 and computers 18 are available for this technique.

In another processing technique, the amplified output signal is first filtered with conventional filters 19, e.g. bandpass filters or high pass filters. Typical filter bandpass could be from 300 kHz to 500 kHz. The filtered signal can then be connected in parallel to a peak detector 20 for recording of initial maximum output signal, a counter 21 for counting the number of impacts, a rate counter 22 for recording the impact rate, and a zero crossing detector 23 to provide the pulse period of the initial output pulse. A converter 24 can also be connected in parallel to the output of the filter 19. In its simple form, the converter 24 could be a standard TRUE RMS meter which contains a suitable integrating time.

SPECIFIC EMBODIMENT

A more complete understanding of the present invention may be had by referring to the following specific embodiment in which the transducer device consisted of a 0.85 inch diameter (shrink tube) housing 1 with a thickness of approximately 0.05 inches and a length of approximately 5.0 inches. No wear surface material 3 was utilized. The front surface element 2 was lead, approximately, 0.75 inches in diameter and 0.75 inches in length. The liquid medium 4 was Sperry Ultrasonic grease (light viscosity type 50A 4086) that comprised a cylindrical volume with the dimensions of 0.75 inches diameter and 1 inch in length. The sensing element 5 was a plastic piezoelectric electret material approximately 0.5 inches in diameter and 0.001 inches in thickness. The electret was bonded to the back surface element 9 using a thin coating (approximately 0.001 inches thick) of Dynaloy 320 conductive epoxy 6. An electrical lead 7 was also bonded to the front side of the sensing element 4 using Dynaloy 320 conductive epoxy. A zinc rod approximately 0.375 inches in thickness and 2 inches in length was used as the back surface element 9. An epoxy damping material 10 (Hysol Epoxy Patch) was bonded to the outside of the back surface material 9 and the external housing 1. An electrical lead 8 was soldered to the back surface 9 material. An electrical connector 12, was soldered to the electrical leads 7 and 8. The electrical connector was bonded to the rear surface of the transducer using Devcon 5 Minute Epoxy. Devcon 5 Minute Epoxy was also used to seal the liquid medium 5 inside the transducer housing 1 by bonding the external housing 1 shrink tubing to the lead front surface element 2. No amplifier 11 was placed internally in the transducer but an amplifier 13 (Kistler Model 557M115) was connected to the connector 12. An external DC powered (Kistler 548D) coupler was used as the external constant current supply 14. The output of connector 12 was then connected by a microdot coaxial cable to a wideband oscilloscope (10 MHz frequency response).

The transducer device was placed in the test section of a two-stage light gas gun where the front surface was first impacted with nylon spheres of 0.50 millimeters diameter and then with nylon spheres of 0.84 millimeters in diameter. The spheres were launched to provide an impact velocity of 4800 feet per second. The peak output voltage of the first pulse appearing on the oscilloscope resulting from the 0.50 mm spheres was approximately 6 millivolts and for the 0.84 mm spheres was approximately 20 millivolts.

The pulse duration of the first positive pulse resulting from impact of the 0.50 mm spheres was slightly less than the same pulse resulting from the impact of the 0.84 mm spheres.

Additional tests establish a correlation between the output voltage $E_n$ and the momentum of the impacting particles where velocities ranged from 3,000 to 12,000 feet per second and the mass of the particles ranged from 0.18 to 1.4 milligrams. The following approximate relationship was obtained empirically.

$$E_n \approx m^k v^L$$

where, $m$ = mass $v$ = velocity $k$ is a constant with a value less than 1.

$L$ is a constant with a value less than or equal to 2.

Preliminary tests with the specific embodiment described above establish $k$ equal to approximately 0.8. Hence, by knowing the velocity and output voltage, impacting mass can be found. By knowing output voltage and mass, impacting velocity can be obtained.

Experimental results indicate that the initial pulse width of the output voltage is somewhat dependent on the impulse I of the impact, that is, $I = mV$; hence, velocity and momentum may also be obtained in a manner similar to above.

Definition of the values of "high" and "low" for wave velocity ($C_L$), acoustic impedance (W), and attenuation ($\alpha$) are used in a "relative" meaning in this patent application. These values can vary somewhat depending upon intended environmental usage or application. In general, however, these values can be defined as follows:

"Low" $C_L$ is less than $3 \times 10(3m/s)$;

"High" $C_L$ is greater than $3 \times 10(3m/s)$;

"Low" W is less than $10(7kg/m^2s)$;

"High" W is greater than $10(7kg/m^2s)$;

"Low" $\alpha$ is less than $10(-2dB/mm)$;

"High" $\alpha$ is greater than $10(-2dB/mm)$.

An example of a typical environment which causes a design constraint on a transducer component and also changes the general definition of the values of "high" and "low" is as follows: The front surface 2 of the transducer must not crack from high energy particle impacts (for example, 1 mg particle impacting at 4000m/s) or melt at high temperatures (for example 100° C). Here, only a limited number of materials such as steel, aluminum, lead, brass, etc. can be used for the front surface element 2. In this case, the values can be defined for the front surface 2 material as:

"Low" $C_L$ is less than $4 \times 10(3m/s)$;
"High" $C_L$ is greater than $4 \times 10(3m/s)$;
"Low" W is less than $3 \times 10(7kg/m^2s)$;
"High" W is greater than $3 \times 10(7kg/m^2s)$;
"Low" $\alpha$ is less than $10(-2dB/mm)$;
"High" $\alpha$ is greater than $10(-2dB/mm)$.

Having thus described my invention with the detail and the particularity as required by the patent laws, what is desired protected by Letters Patent is set forth in the following claims.

I claim:

1. A transducer device comprising:
   a housing comprising a material of low elastic wave propagation velocity and high wave attenuation properties;
   a front surface element mounted at one end of said housing, said front surface element having a front surface arranged to accept mechanical energy for creating an elastic wave therein, said front surface element comprising a material having high elastic wave attenuation properties;
   a rear surface element mounted relative to said housing and spaced from said front surface element, said rear surface element comprising a material having high elastic wave attenuation properties;
   a thin transducer element mounted upon the rear surface element between the rear surface element and the front surface element; and
   means between the front surface element and the thin transducer for transmitting elastic waves but which means does not transmit transverse elastic waves,
   whereby a characteristic of the electrical signal output of said thin transducer element is related to the first and the fastest elastic wave created at the front surface of said front surface element.

2. A system for monitoring particles in a particle flow stream comprising:
   a transducer device according to claim 1 arranged with the front surface in the path of said flow stream;
   means for processing the electric signal output of said thin transducer to produce an output signal indicative of a characteristic of the particles impinging the front surface.

3. A system according to claim 2 wherein said processing means detects the peak voltage of an output pulse of the thin transducer resulting from a particle impacting the front surface, said peak voltage being characteristic of the energy, mass, size and/or velocity of said impacting particle.

4. A system according to claim 2 wherein said processing means detects the initial pulse width of an output pulse of the thin transducer resulting from a particle impacting the front surface, said pulse width being indicative of velocity and/or momentum.

5. The system according to claim 2 wherein the processing means comprises a means for recording said thin transducer output signal.

6. The system according to claim 2 wherein the processing means filters the output of said thin transducer to pass only a signal corresponding to the first pulse resulting from a particle impacting the front surface.

7. The system according to claim 6 wherein the center frequency of the band passed by said processing means is approximately 500 kHz.

8. The system according to claim 6 wherein the processing means integrates the filtered signal over a selected time interval to provide a DC output.

9. The system according to claim 6 wherein the means for processing comprises means for counting the pulses in the filtered signal, said count being indicative of the number of particles striking the front surface.

10. The system according to claim 6 wherein the means for processing comprises means for measuring the rate of pulses in the filtered signal, said rate being indicative of the rate of impact of particles on the front surface.

11. A transducer device comprising:
    a housing comprising a material of low elastic wave propagation velocity and high elastic wave attenuation properties;
    a front surface element mounted at one end of said housing, said front surface element having a front surface arranged to accept mechanical energy for creating an elastic wave, said front surface element comprising a material having high elastic wave attenuation properties;
    a rear surface element mounted relative to said housing and spaced from said front surface element, said rear surface element comprising a material having high elastic wave attenuation properties;
    a thin piezoelectric transducer element mounted upon the rear surface element between the rear surface element and the front surface element;
    a damping material surrounding the rear surface element filling the space between the rear surface material and the housing; and
    liquid means between the front surface element and the thin transducer element for transmitting elastic waves but which does not transmit transverse elastic waves,
    whereby a characteristic of the electric signal output of said thin transducer is related to the first and the fastest elastic wave created at the front surface of said front surface element.

12. A transducer device according to claim 11 wherein a thin coating of a wear resistant material covers the front surface of the front surface element.

13. A transducer device according to claim 11 wherein the thin piezoelectric transducer is selected from a group comprising flourinated ethylene, polyvinylflouride and tetrafluoroethylene electrets with electrodes on each face.

14. A transducer device according to claim 11 wherein the liquid means comprises a material selected from the group consisting of water, grease and oil.

15. A transducer device according to claim 11 wherein the front surface material is lead.

16. A transducer device according to claim 11 wherein the back surface material is selected from the group comprising zinc, lead, plastic and rubber.

* * * * *